United States Patent
Voit et al.

(10) Patent No.: US 8,997,800 B2
(45) Date of Patent: Apr. 7, 2015

(54) APPARATUS AND PROCESS FOR REMOVING SUBSTANCES FROM PRE-FILLED CONTAINERS

(75) Inventors: Thomas Voit, Hilden (DE); Andrea Wildhaber, Neuhaus (SE)

(73) Assignee: Qiagen GmbH, Hilden (DE)

( * ) Notice: Subject to any disclaimer, the term of this patent is extended or adjusted under 35 U.S.C. 154(b) by 1394 days.

(21) Appl. No.: 12/673,758

(22) PCT Filed: Aug. 18, 2008

(86) PCT No.: PCT/EP2008/060810
§ 371 (c)(1),
(2), (4) Date: Mar. 22, 2011

(87) PCT Pub. No.: WO2009/024559
PCT Pub. Date: Feb. 26, 2009

(65) Prior Publication Data
US 2011/0162755 A1    Jul. 7, 2011

(30) Foreign Application Priority Data

Aug. 17, 2007 (EP) ..................................... 07016192
Sep. 24, 2007 (EP) ..................................... 07018725

(51) Int. Cl.
*B65B 3/04* (2006.01)
*G01N 35/10* (2006.01)
*B01L 3/00* (2006.01)

(52) U.S. Cl.
CPC ........ *G01N 35/1079* (2013.01); *B01L 3/50853* (2013.01); *B01L 2200/16* (2013.01); *B01L 2300/044* (2013.01); *B01L 2300/0672* (2013.01); *B01L 2300/0832* (2013.01)

(58) Field of Classification Search
USPC ............. 141/65, 311 R, 329–330; 435/288.4; 73/863.85, 864.74, 864.01, 863.32; 422/916, 501, 512, 546, 551–553; 604/403, 411, 415
See application file for complete search history.

(56) References Cited

U.S. PATENT DOCUMENTS 4,286,637 A * 9/1981 Wilson .......................... 141/374
4,577,514 A    3/1986 Bradley et al.
(Continued)

FOREIGN PATENT DOCUMENTS

DE          19512607        10/1996
DE        102004038152       2/2006
(Continued)

OTHER PUBLICATIONS

International Search Report of PCT/EP2008/060810, completed Nov. 28, 2008.

*Primary Examiner* — Timothy L Maust
*Assistant Examiner* — Timothy P Kelly
(74) *Attorney, Agent, or Firm* — Miles and Stockbridge (57) ABSTRACT

A system (10) for removing a pipettable substance from a pre-filled container (20), which is closed off by a top (30) having at least one opening area (40), comprises an opening tool (100) having a tube (110), which has a cross-section corresponding substantially to the shape of the opening area and which comprises at a distal end (120) an endpiece (140) extending substantially obliquely relative to the longitudinal axis of the tube, which moves a part of the top (30) located inside the opening area (40) towards the container when the opening tool is applied, so as to form an opening in the top, and a point of attack (150) for a transporting tool (200). The opening tool (100) is designed to remain on the container (20) after use. Moreover, the system comprises a transporting tool (200) for moving the opening tool (100) through the top, and a cannula (250), which is adapted to be inserted over at least part of its length through the tube (110) into the interior of the container (20), in the position of use of the opening tool (100), and one end of which can be connected to a suction device (300) for sucking a pipettable substance out of the interior of the container (20).

17 Claims, 9 Drawing Sheets

(56) References Cited

U.S. PATENT DOCUMENTS

| | | | |
|---|---|---|---|
| 4,721,137 A * | 1/1988 | Muller | 141/65 |
| 4,808,381 A * | 2/1989 | McGregor et al. | 422/512 |
| 4,935,020 A * | 6/1990 | Broden | 604/411 |
| 4,982,740 A | 1/1991 | Broden | |
| 6,027,694 A * | 2/2000 | Boulton et al. | 422/553 |
| 6,475,774 B1 | 11/2002 | Gupta | |
| 6,500,390 B1 * | 12/2002 | Boulton et al. | 506/43 |
| 7,413,910 B2 * | 8/2008 | Kearney et al. | 436/180 |
| 8,337,779 B2 * | 12/2012 | Miyashita | 422/512 |
| 8,518,350 B2 * | 8/2013 | Denawa et al. | 422/552 |
| 2006/0263250 A1 | 11/2006 | Blouin et al. | |

FOREIGN PATENT DOCUMENTS

| | | |
|---|---|---|
| EP | 0126390 | 11/1984 |
| EP | 0478905 | 4/1992 |
| WO | 89/12829 | 12/1989 |
| WO | 90/11752 | 10/1990 |
| WO | 2005/100945 | 10/2005 |

* cited by examiner

APPARATUS AND PROCESS FOR REMOVING SUBSTANCES FROM PRE-FILLED CONTAINERS

This application is a §371 National Stage Application of PCT/EP2008/060810 filed Aug. 18, 2008, which claims priority to European Application 07016192.2 filed Aug. 17, 2007 and European Application 07018725.7 filed Sep. 24, 2007.

BACKGROUND OF THE INVENTION

1. Field of the Invention

The present invention relates to an apparatus for removing substances from pre-filled containers. The apparatus is suitable for example for applications in biochemistry, molecular genetics, microbiology, medical diagnostics or forensic medicine.

2. Description of Related Art

In numerous technical fields such as chemistry, biology, biochemistry, biotechnology, medicine or environmental technology it is necessary to analyse, separate, process or react materials containing biological target molecules (e.g. pourable biological samples). For this purpose the liquids or materials are filtered, cooled, heated, broken down into their components, washed or pipetted by various methods and/or treated by other methods. It is often necessary to go through a long and complex sequence of processing steps in order to prepare the biological material. During processing, various reagents are added. Depending on the nature of the analysis or the preparation of the sample, different combinations of reagents are used during the process. Particularly for larger quantities of sample the processing is typically automated. Usually, the reagents needed for the processing are held in pre-filled containers and placed by an operator in an apparatus for automatic sample processing. In order to remove the reagents the apparatus is provided with means for opening the containers—if these have not already been opened during the loading of the apparatus—and for controlled removal. The opening and removal may be done by the same tool, for example by pushing a cannula through a perforatable top of the container and then sucking out the reagent using an external suction device.

A number of variants are known for removing pipettable substances from pre-filled containers. However, the prior art leaves plenty of room for improvement. The objective of the present invention is therefore to construct an apparatus of this kind with a view to improving the processing efficiency and economy.

SUMMARY OF THE INVENTION

In one aspect the invention relates to a system for removing a pipettable substance from a pre-filled container sealed off with a top having at least one opening area, comprising an opening tool with a tube which has a cross-section corresponding substantially to the shape of the opening area and which comprises at a distal end a closure extending substantially at an angle relative to the longitudinal axis of the tube, which moves a part of the top located inside the opening area towards the container when the opening tool is applied, so as to form an opening in the top. In addition, the opening tool has a point of attack for a transporting tool, the opening tool being designed to remain on the container after use, a transporting tool for moving the opening tool through the top, and a cannula which is adapted to be inserted over at least part of its length through the tube into the interior of the container, in the state of use of the opening tool, and one end of which can be connected to a suction device for sucking a pipettable substance out of the interior of the container.

DETAILED DESCRIPTION OF A PREFERRED EMBODIMENT

Typically the opening area is substantially of a shape selected from among a circle, ellipse or polygon. It is also typically characterised by one or more of the features selected from the following group:
- the opening area has a substantially lesser material thickness than the top,
- the opening area consists of a different material from the top,
- the opening area is confined by a boundary region which substantially has a lesser material thickness than the top, the boundary region typically having areas of different material thickness,
- the opening area is confined by a boundary region of greater material thickness than the top.

Typically, the opening tool comprises at least one positioning element for exact positioning on the container, selected from among a pin, hole, slot, groove and ridge.

Typically, the inclined endpiece of the tube of the opening tool has a point at its distal end and has at least two different angles $\alpha$ relative to the longitudinal axis of the tube over the area from its dorsal end to its distal end. Typically the angle $\alpha$ of the slant of the endpiece of the tube relative to the longitudinal axis of the tube in the region of the distal end of the endpiece is substantially smaller than in other areas of the endpiece.

Typically, one end of the tube ensures a friction-locked engagement of the tube in the top of the container with the opening tool in its applied position, typically by a construction in the shape of a cone.

Typically, a plurality of tubes are arranged in an m×n matrix and connected by a common element. Typically, a spatial direction defined by a perpendicular to the main plane of the inclined endpiece of the tube is different in at least two of the tubes.

In another aspect the invention relates to a container for providing pipettable substances which comprises a plurality of similar or differently shaped chambers each having at least one opening and at least one top for closing off the openings, and cone-like guides formed in the at least one top.

Typically, the container comprises a positioning element selected from among the group comprising a pin, a hole, a slot, a groove and a ridge.

Typically, the at least one top of the container is provided with at least one opening area.

Typically, the opening area of the top of the container essentially has a shape selected from among a circle, ellipse and polygon. The opening area is moreover typically characterised by one or more of the features selected from the following group:
- the opening area has a substantially lesser material thickness than the top,
- the opening area consists of a different material from the top,
- the opening area is confined by a boundary region which substantially has a lesser material thickness than the top, the boundary region typically having areas of different material thickness,
- the opening area is confined by a boundary region of greater material thickness than the top.

Typically the container is filled with substantially all the substances required for a predetermined process, particularly for processing, purifying and/or analysing materials containing biological target molecules.

In another aspect the invention relates to an opening tool for a pre-filled container closed off by a top which has at least one opening area, the opening tool comprising a tube which has a cross-section corresponding substantially to the shape of the opening area and at a distal end an endpiece extending substantially at an angle relative to the longitudinal axis of the tube, which moves a part of the top located inside the opening area toward the container when the opening tool is applied so as to make an opening in the top in this way, the inclined endpiece having a point at its distal end and having at least two different angles α relative to the longitudinal axis of the tube over the area from its dorsal end to its distal end.

Typically, the angle α of the slant of the endpiece of the tube relative to the longitudinal axis of the tube in the region of the distal end of the endpiece is substantially smaller than in other areas of the endpiece.

Typically, a tube of the opening tool comprises a retaining element for fixing the opening tool to the container, typically in the form of a shoulder or groove that at least partly encircles the tube.

Typically, one end of the tube ensures a friction-locked engagement of the tube in the top with the opening tool in its applied position, the tube typically being in the shape of a cone over at least part of its length.

Typically a plurality of tubes of the opening tool are arranged in an m×n matrix and connected by a common element. Typically, a spatial direction defined by a perpendicular to the main plane of the inclined endpiece of the tube is different in at least two of the tubes.

In another aspect the invention relates to a process for removing a pipettable substance from a pre-filled container, comprising the steps of:
a) providing a system according to the invention and a container according to the invention,
b) automated or manual application of an opening tool according to the invention to a top of the container,
c) moving the opening tool through the top of the container so that a tube of the opening tool at least partly opens an opening area in the top of the container and the tube penetrates into the interior of the container, over at least part of its length, and is fixed therein,
d) positioning a pipetting tool in a position above a through-opening in the opening tool and lowering the pipetting tool into the through-opening and into the tube below, until at least part of the pipetting tool projects from the distal end of the tube into the substance that is to be removed,
e) sucking up a pipettable substance contained in the container through the pipetting tool by means of a suction device connected thereto.

Typically the process comprises an additional step f) in the form of the total withdrawal of the cannula from the opening tool.

Typically, steps d) to f) are repeated several times, using the same or different cannulas.

Typically, the movement in step c) is accompanied by the engagement of positioning elements between the container and the opening tool, which are selected from among the group comprising pin-hole, pin-slot and groove-ridge.

Typically steps d) to f) are carried out using a plurality of pipetting tools at the same time.

Typically the container used in the process has a number of separate chambers, each of which has an associated opening area in a top. Typically in step c) a plurality of tubes open a plurality of opening areas at least in part as the opening tool is moved.

Typically the process comprises a further step g) in which the container with the opening tool applied is closed off by means of a cover arranged on the opening tool.

Typically in step b) the opening tool is centred on the top by means of typically conically shaped guides.

In view of the above remarks a system according to claim 1, a container according to claim 10, an opening tool according to claim 16 and a process according to claim 22 are provided.

The details of the invention will be explained more fully hereinafter with reference to various embodiments, referring to the accompanying drawings, wherein.

Figure 1A:
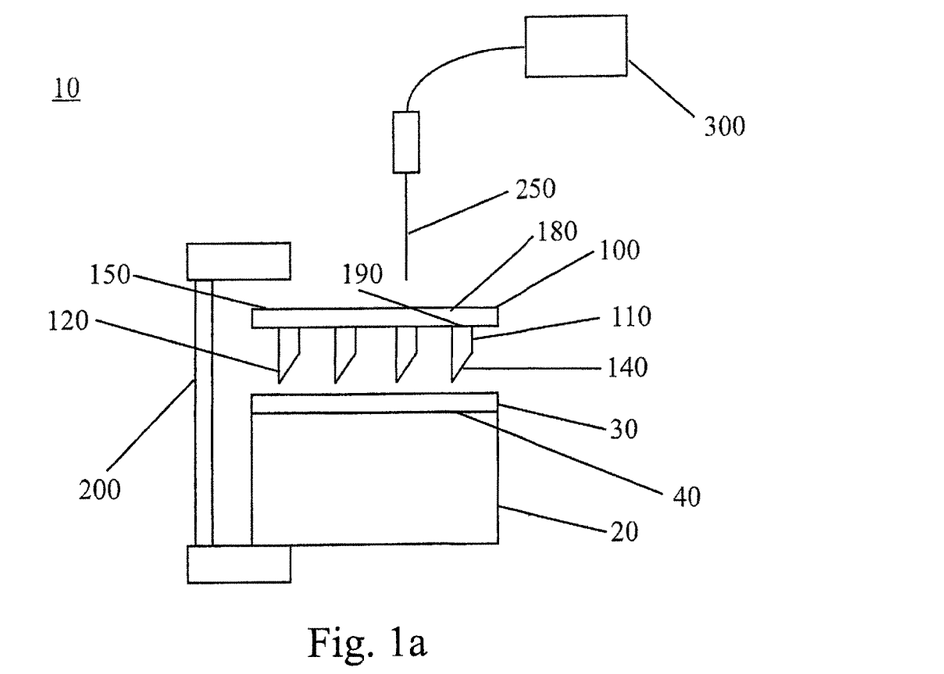
FIGS. 1a-1b show schematic views of a system according to one embodiment

FIG. 1a schematically shows a preferred embodiment of a system according to the present invention. A container (20) pre-filled with pipettable substances (reagents) is closed off by a top (30). This top has at least one opening area (40). An opening tool (100) comprises at least one tube (110) which has a cross-section corresponding substantially to the shape of the opening area and at its distal end (120) an endpiece (140) (hereinafter also referred to as the cutting edge) that extends substantially obliquely relatively to the longitudinal axis of the tube. To prepare for the application of the opening tool the latter is placed on the top of the container so that the endpiece of the tube (110) is resting on the opening area. In order to open it the opening tool and the container (20) are pressed together, typically by means of a transporting tool (200), which engages on at least one point of attack (150) on the opening tool and/or on the container. Typical embodiments of a transporting tool of this kind are known to the skilled man.

In particular, the opening tool (100) and/or the container (20) may each be equipped with at least one positioning element for accurate positioning on the transporting tool (200). Typically, elements are selected from a group comprising pins, holes, slots, grooves and ridges. One or more positioning elements of the transporting tool (200) engage, during the pressing process, with a mating positioning element, as a counterpart, which is provided on the container and/or on the top (30). Corresponding possible pairs are pin and hole, pin and slot, groove and ridge or pin and groove, while combinations of other elements may also be regarded as falling within the scope of the invention.

Figure 3A:
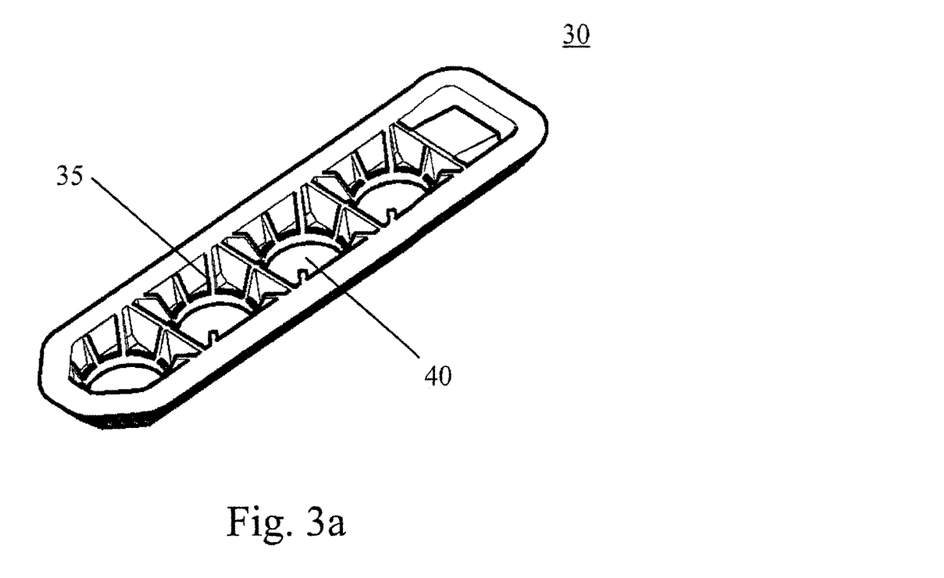
FIGS. 3a-3b show a perspective view and lateral cross-sectional view of a top according to one embodiment
Figure 3B:
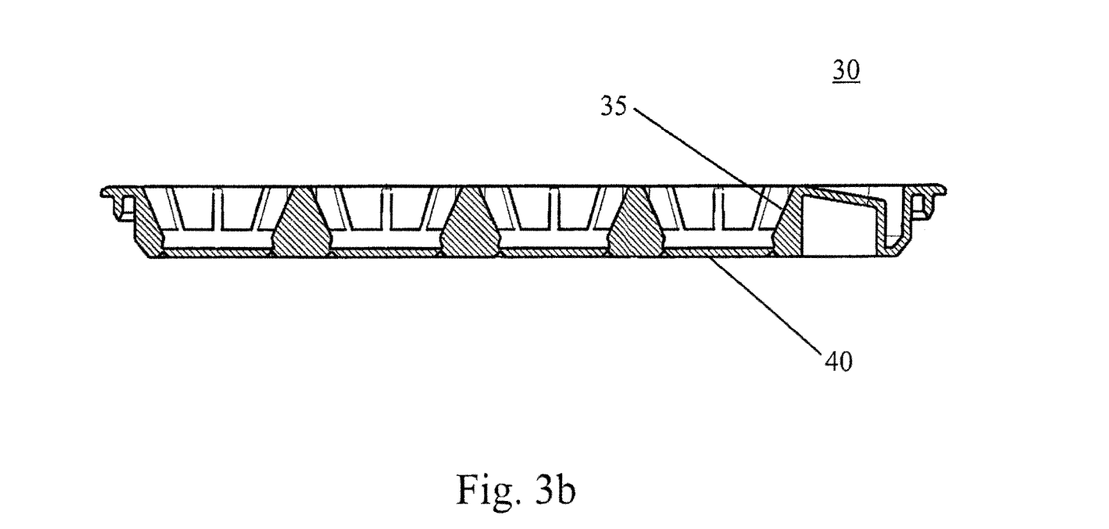

During the opening, a part of the top (30) located inside the opening area (40) is moved by the pressure of the endpiece of the tube towards the container (20) and in this way an opening is made in the top (30). FIGS. 3*a* and 3*b* show a preferred embodiment of the top. At the same time the tube penetrates through the opening into the interior of the container. The opening tool (100) remains on the container (20) after the opening process described above.

A stable positioning of the tool in the container can be ensured by a number of different methods. In a preferred embodiment the opening tool lodges in the top (30) of the container (20) by mechanical frictional engagement. Another variant comprises a retaining element, e.g. a shoulder (175) or groove running around the outside of the tube and engaging with the top (30) of the container (20). The shoulder and other details are not shown in FIGS. 1*a* and 1*b* for reasons of clarity; an illustration of the shoulder (175) by way of example is to be found in FIGS. 7*c* and 7*d*. The shoulder or groove may extend continuously or over only parts of the outside of the tube.

Figure 1B:
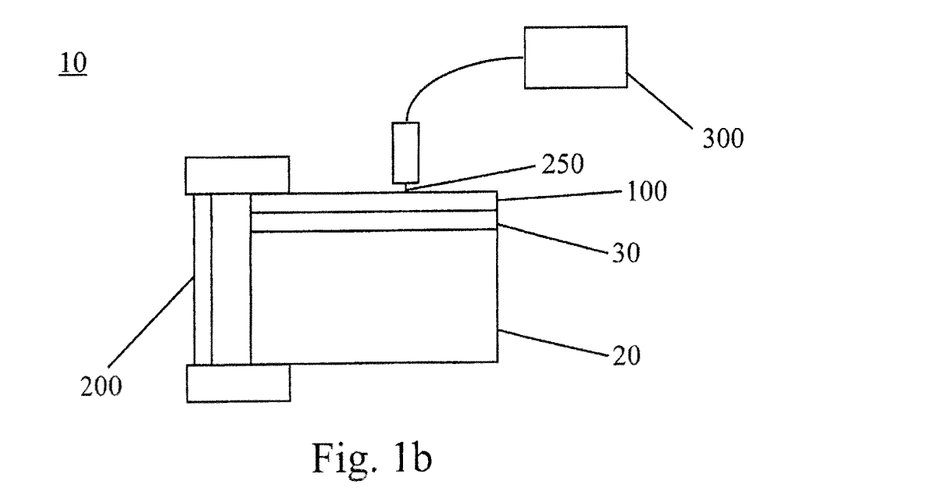

In order to remove the pre-filled substance a pipetting tool (250) is then inserted, at least over part of its length, through a through-opening (190) in the tube (110) of the opening tool into the interior of the container (20) until at least part of the pipetting tool protrudes out of the distal (lower) end (120) of the tube into the substance that is to be removed. The pipetting tool is connected to a suction device (300) which is designed to suck up a pipettable substance from the interior of the container (20). The pipetting tool can be inserted both by means of actuators, which are typically operated by automatic control, and manually, and this also applies to later withdrawal of the pipetting tool from the container or tube. FIG. 1*b* schematically shows the system with the opening tool (100) applied and a pipetting tool (250) which has been inserted in the container.

Using the pipetting tool, the end of which protrudes into the substance to be pipetted in the pre-filled container (20), the substance is then removed from the container by means of the suction device (300). Either some or all of the contents of the container can be removed in one operation. For example, using the pipetting tool, some of the contents can be removed, the pipetting tool can be withdrawn completely from the container (e.g. retracted) and moved into a parking position, for example. At a later time more of the contents of the container can then be removed using the same or a different pipetting tool.

The advantage of the present invention over known systems in the prior art is that the process of opening the top and removing the pipettable substance are carried out separately. This prevents the sharp end of the pipetting tool, which is used to pierce the top in systems known from the prior art, from becoming blocked or damaged. At the same time the demands made of the mechanical stability of the pipetting tool are reduced as it does not have to transmit the force needed to open the top. Moreover, by separating the opening tool and the pipetting tool it is also possible to detect the level of pipettable substance remaining in the container through the opening, as the opening is still there even after the pipetting tool has been withdrawn. Other embodiments of the invention relate to further features of the opening tool and top which allow easier, reliable opening.

If the pipetting tool has been removed completely from the container after one or more removal processes and no further substances are to be removed at this stage, the container (20) with the opening tool (100) placed thereon can optionally be resealed by means of a cover in order to prevent any contamination or evaporation of the pre-filled substances. The cover is arranged on the opening tool. The nature of the cover is not particularly restricted and there are numerous possible embodiments known from the prior art such as foils, covers made of flexible or rigid materials such as plastics, metal or the like. The cover may be intended for both single and repeated use.

Figure 2A:
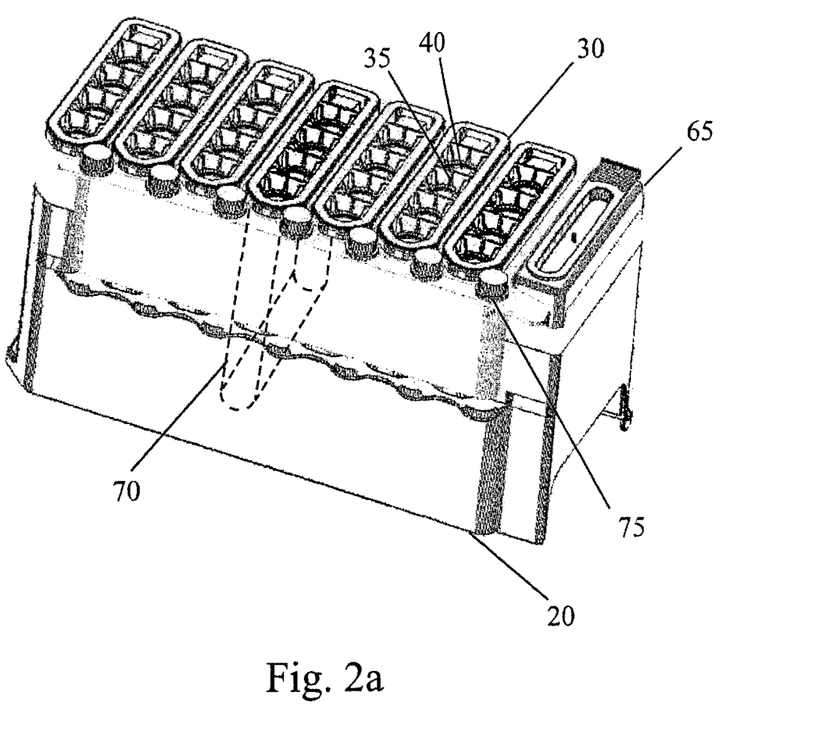
FIG. 2a shows a perspective view of a container without an opening tool according to one embodiment

FIG. 2*a* shims a container (20) according to one embodiment of the invention. The container may comprise a plurality of chambers or inserts (70) which are constructed to be separate from one another, of identical or different shapes, each having at least one opening. In the Figure, a chamber (70) is schematically represented by dotted lines, by way of example. In a typical application of the invention, the container (20) comprises several (in this case seven) chambers or inserts (70) which are filled with substantially all the substances required for a particular processing operation, particularly for processing, separating and/or analysing a material containing a biological target molecule. These include, for example, one or more lysing solutions, washing solutions, eluting solutions, buffers, binding solutions, separating materials in pipettable form such as suspensions of magnetic beads, enzymes, probes, markers, starting materials for downstream applications such as PCR, arrays and/or assays and the like.

In the embodiment described, the chambers or inserts (70) are typically provided with the lids (30) described in more detail hereinafter. Besides the chambers, the contents of which are removed using the process or system according to the invention, the container may comprise further chambers and/or inserts (65, 75), which typically also contain materials for carrying out the planned processes, but wherein the contents are not removed by means of the process or system according to the invention. Thus, some of the materials mentioned above by way of example may be located in the chambers or inserts (70), whereas other required substances are advantageously introduced into the remaining chambers and/or inserts of the container. It is particularly advantageous if the one or more lysing solutions, washing solutions, eluting solutions, binding solutions and/or buffers are contained in the chambers (70).

The use of inserts that can be introduced into the container and taken out of it again has the advantage that materials requiring special treatment, such as enzymes which have to be refrigerated, or suspensions that have to be homogenised again immediately before use, can undergo their special treatment independently of the other materials and the container as a whole.

Figure 2B:
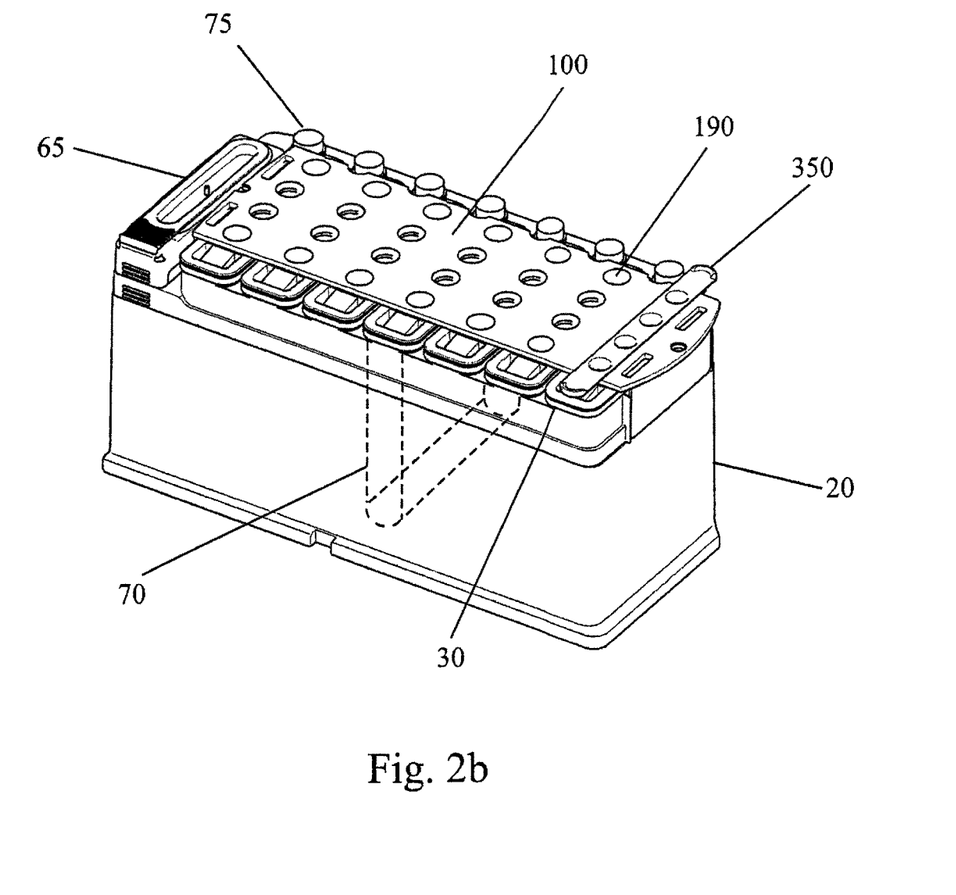
FIG. 2b shows a perspective view of a container with an opening tool according to one embodiment

The chambers in the embodiment shown in FIG. 2*b* are each provided with a top (30) to which the opening tool (100) is applied. In the figure a chamber (70) is schematically shown by dotted lines, by way of example. The through-openings (190) made by the opening tool allow the pipetting tool to be introduced into the chamber or insert (70). FIG. 2*b* also shows a cover (350), which is applied only to one of the lids, by way of example. The cover may advantageously be used repeatedly and is typically made from a resilient plastics material.

FIG. 3*a* shows a perspective view of a top (30) for the container (70) according to one embodiment. FIG. 3*b* shows a cross-section through this top (30). The typically conically shaped guides (35) over the opening areas (40) advantageously have a guide function for the tubes (110) of the opening tool (100), so that the tool is centred as it is applied to the top. One or more opening areas (40) in the top (30) have associated with them one or more underlying chambers (70) of the container (20). In the embodiment shown, four opening areas are provided for one chamber. Depending on the design, the same substance can be taken from one chamber and/or different or identical substances can be taken from a plurality of chambers using a plurality of pipetting tools at the same time through several openings in the top. In the case of a plurality of pipetting tools, corresponding adaptation of the suction device (300) may be necessary, or a number of suction devices may be used.

Figure 4A:
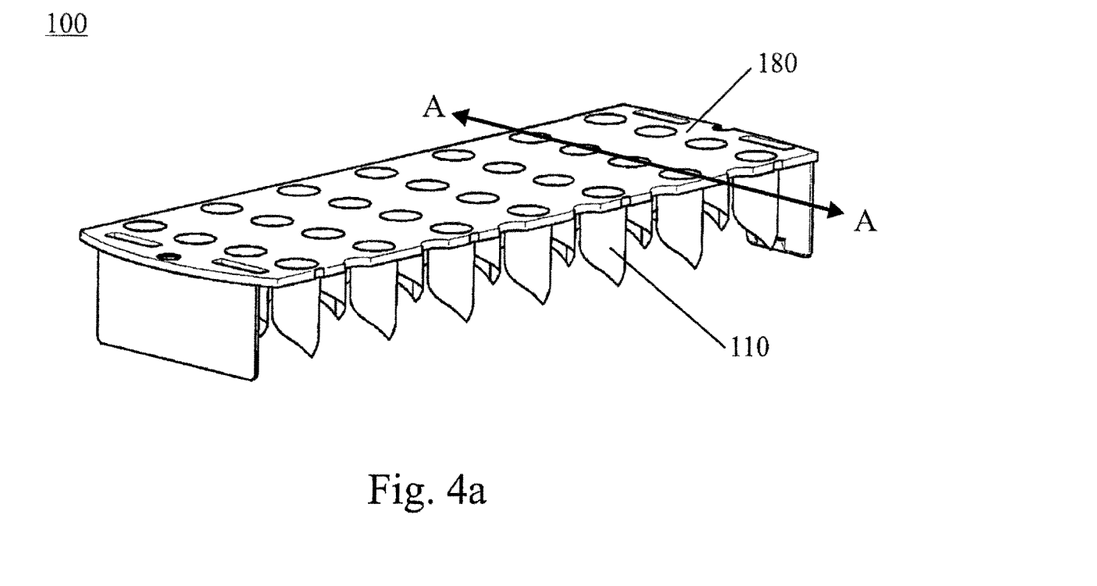
FIGS. 4a-4b show a perspective view and cross-sectional view of an opening tool according to one embodiment

FIG. 4a shows a preferred embodiment of the opening tool (100) which comprises a plurality of tubes (110) arranged in an m×n matrix and connected by an element (180). The tubes (110) of the opening tool are typically at different angular positions relative to their longitudinal axes. In other words, the spatial direction defined by the perpendicular to a main plane of the slanting endpiece (140) of the tube (110) differs from one individual tube to another. By the main plane is meant the plane which, in the understanding of a skilled man, is most suitable for representing the direction of the endpiece.

Typically the angular positions of the perpendiculars between the individual tubes differ by multiples of 90°, giving four different possible angular positions. This ensures guiding and centering of the opening tool when it is applied to or placed on the top (30) by means of typically conically shaped guides (35).

Figure 4B:
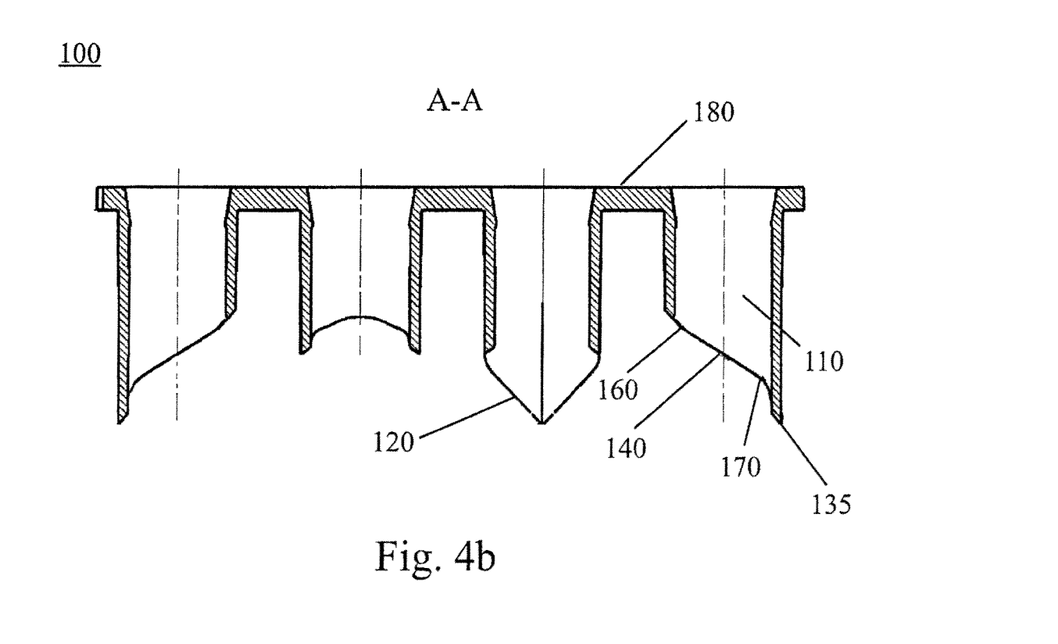

FIG. 4b shows a cross section through the opening tool of FIG. 4a along the stretch A-A, wherein the different sectional profiles of the tubes are shown, which are a result of the different angular positions.

In one embodiment of the invention the tube (110) of the opening tool (100) may have a cross sectional shape which is other than circular, such as (as non-restrictive examples) the cross sectional shapes of an ellipse or polygon or any desired variations. In addition, the tube (110) may have a structure which is only substantially tubular but deviates from a tubular shape. These might include for example missing segments or differently shaped openings in the wall structure.

Figure 5A:
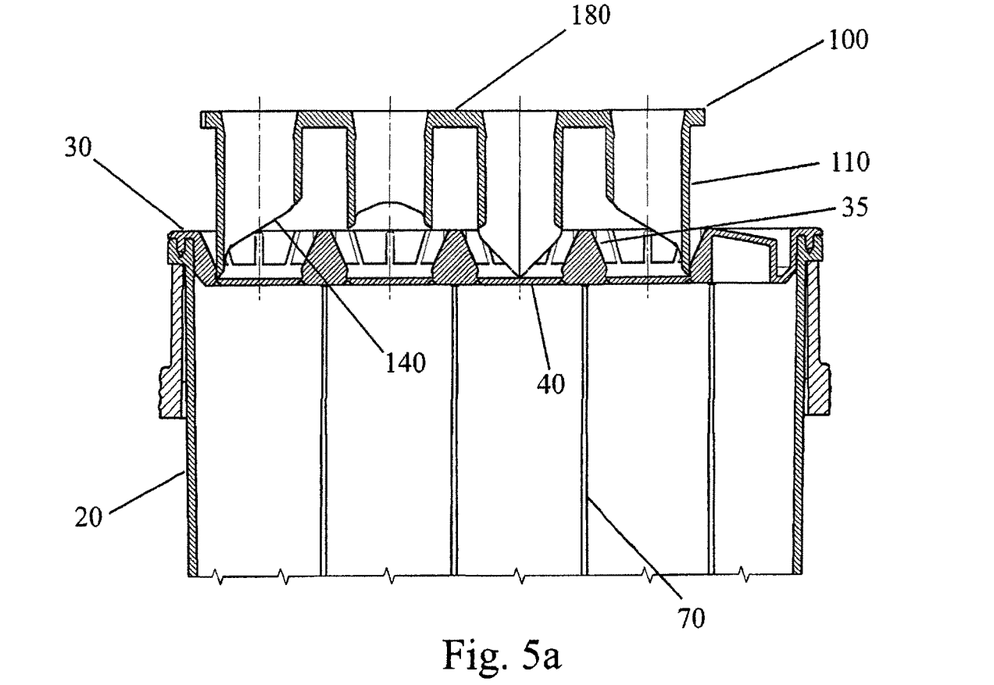
FIGS. 5a-5b show cross-sectional views of a container with a top and opening tool according to one embodiment, before and after the opening process
Figure 5B:
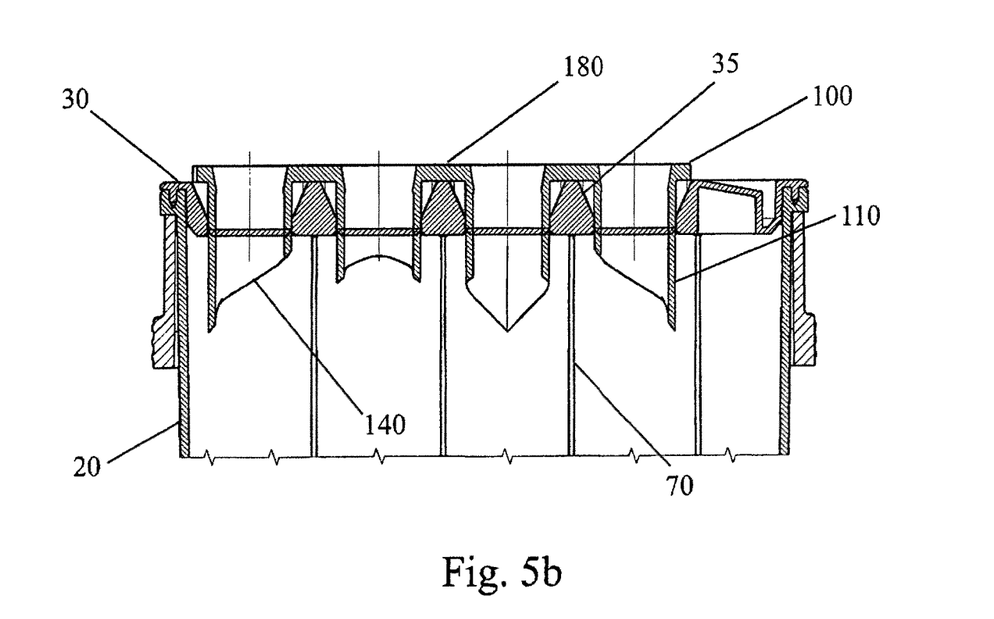

FIG. 5a shows a container (20) with its associated top (30) and opening tool (100) placed thereon, according to a preferred embodiment. The tips of the tubes (110) are located on the opening areas (40) of the top (30). Technical measures may be taken to prevent the positioned opening tool from accidentally damaging or perforating the opening areas of the top. The conical guides (35) centre the tubes (110) and hence the opening tool (100) in relation to the top. FIG. 5b shows the position after the opening tool (100) has been pressed through the top (30). The opening areas (40) cut out by the cutting edges (140) are not shown in FIG. 5b.

As already shown, as the opening tool is moved or pressed in the direction of the opening areas, a part of the top (30) located inside the opening area (40) is moved in the direction of the container and in this way an opening is made in the top. The slanting endpiece (140) of the tube (110), acting as a kind of cutting edge, exerts a force on the opening area. In one embodiment of the invention the entire opening area (40) has a substantially lesser material thickness than the remainder of the top (30), in order to facilitate the opening process. In another embodiment the opening area is made from a different, typically softer material than the rest of the top, in order to assist with cutting open, a process which can be carried out for example using a 2C (2 component) injection moulding process known in the art. The opening area may also be in the form of a foil or film.

Figure 6:
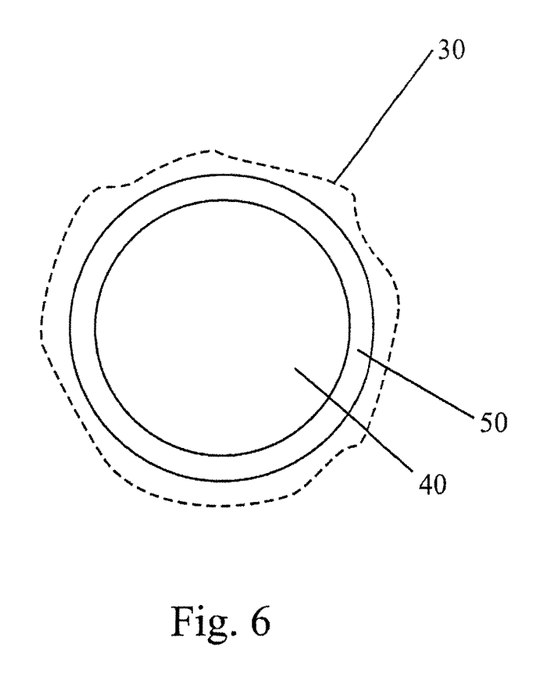
FIG. 6 is a schematic plan view of an opening area of a top according to one embodiment

FIG. 6 shows a detail of a top (30) of the container (20) according to a preferred embodiment of the invention. The opening area (40) is confined by a boundary region (50). The boundary region acts as a kind of frangible point or weakened point, along which the connection between the opening area and the top is to be broken by means of the cutting edge. For this purpose the boundary region is designed so that easy separation is guaranteed using the cutting edge. This can be achieved in various ways.

In a preferred variant the boundary region is constructed so as to have a different, typically lesser material thickness than the rest of the top (30). In another embodiment the boundary region (50) itself has regions of different material thickness. As a non-restrictive example, in a circular boundary region (50), half of the circle may have a material thickness corresponding to a quarter of the thickness of the surrounding top, while the other half has a material thickness of 70% of that of the surrounding top.

In another embodiment the boundary region is made of a different material from the rest of the top, which may be achieved for example using a 2C injection moulding process known in the art. The boundary region may also be in the form of a foil or film, for example.

By bounding the opening area with a region of lesser material thickness it is easier to open using the means according to the invention. In the embodiment mentioned above with a variable thickness of the boundary region (50), an additional effect is achieved. The region of lesser thickness allows easy initial penetration or cutting by means of the endpiece (140) of the tube (110). As the tube increasingly penetrates into the container the boundary region (50) is cut through more and more by the slanting endpiece (140). It is desirable that the opening area should not be totally severed from the rest of the top as otherwise the severed part could fall into the container. This could lead to problems during pipetting if the severed part of the top were to lie in front of the opening of the pipetting tool. The rather thicker region of the boundary region helps to prevent the boundary region from being severed completely. As a result the cut away part of the opening area remains attached to the rest of the top at this point and does not fall into the container (20).

The objective of opening the top with minimum force and preventing total severing of the opening area, as already described above, is also achieved by means of the following embodiments of the invention. The amount of force required is particularly great if a number of opening areas are to be opened simultaneously and if the top is firmly attached to the container, e.g. by welding. In addition, considerable forces are required when using conventional closure materials such as polyethylene to form the top.

Figure 7A:
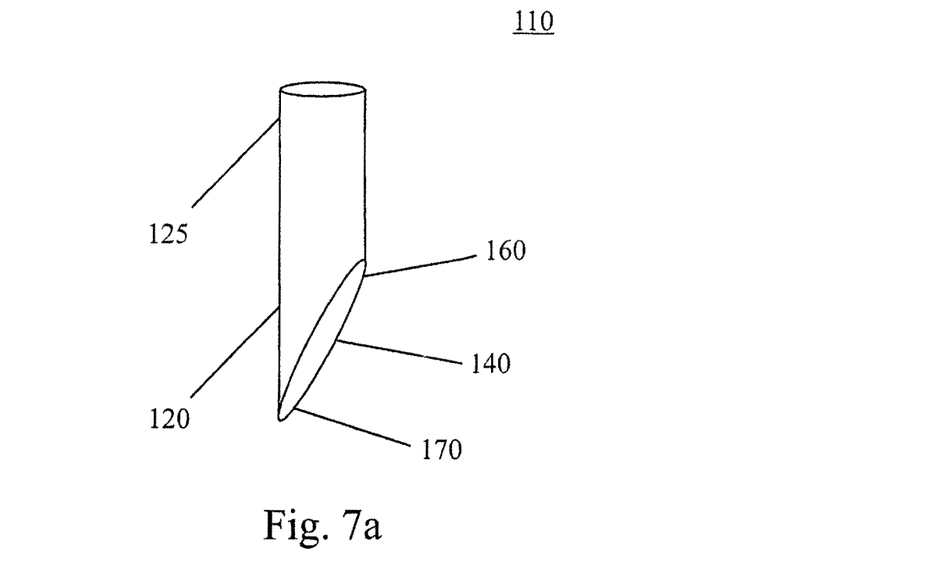
FIGS. 7a-7d are perspective views and a cross-sectional view of rubes an opening tool according to embodiments In the following description of various embodiments of the present invention, functionally similar features of the different embodiments have been given the same reference numerals.

FIG. 7a shows a tube (110) of the opening tool according to one embodiment of the invention. The tube (110) has a dorsal end (125) and a distal end (120). The oblique endpiece (140) (cutting edge) also has a dorsal end (160) and a distal end (170). In this embodiment the angle of the slant (140) is constant.

Figure 7B:
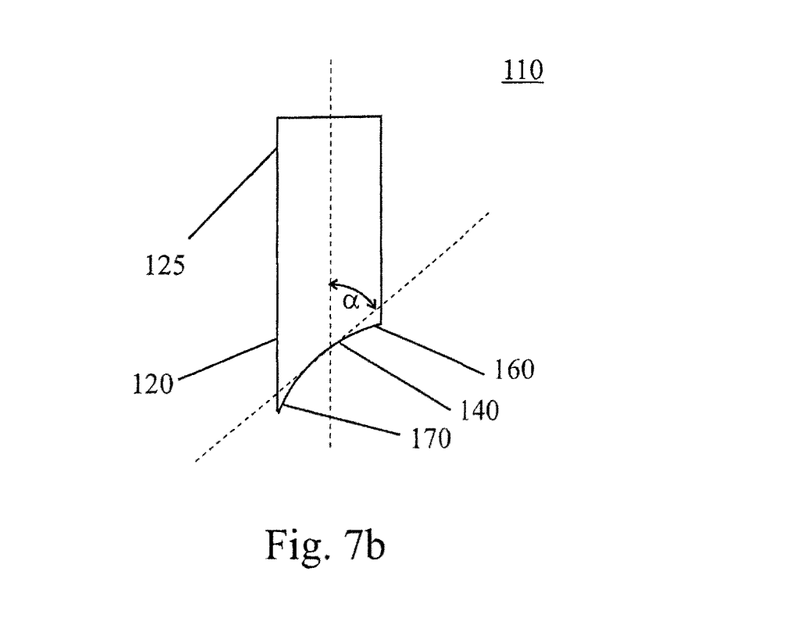

FIG. 7b shows an embodiment of the invention in side elevation, wherein the slant of the endpiece (140) of the tube (110) has at least two different angles α relative to the longitudinal axis of the tube, in the area from the dorsal end (160) to the distal end (170) of the endpiece. Typically the endpiece is constructed so that the smaller angle is in the region of the distal end (170) and the larger angle is in the region of the dorsal end (160). This allows cutting or penetration to take place with reduced application of force compared with an endpiece having a constant slant angle. As a result of the larger angle at the dorsal end (160) the cutting action of the slanting endpiece (140) of the tube in this region is reduced, as a result of which part of the boundary region (50) is not cut through, if the dimensions are suitably chosen. The endpiece (140) of the tube thus acts not as a cutting edge but as a pressing edge at this point, the part of the opening area which has already been cut away being pressed towards the interior of the container.

Figure 7C:
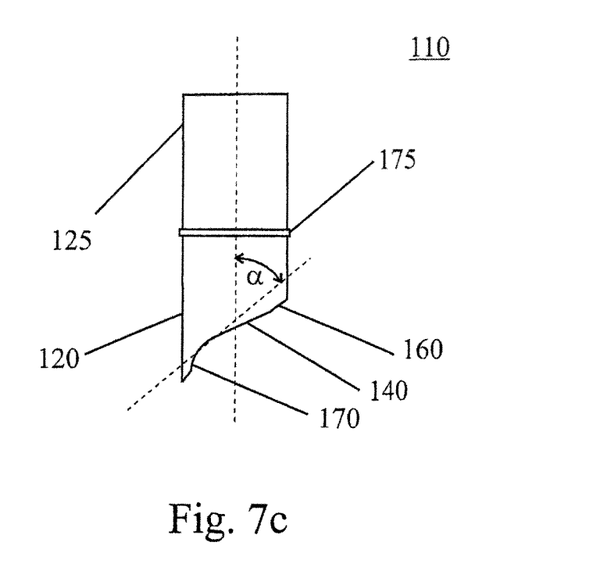

FIG. 7c shows a preferred embodiment of the invention in side elevation, wherein the annular configuration is particularly advantageous for the purpose outlined above. For manufacturing or other reasons it may be expedient for the angle of the slant to be somewhat larger over a short section in the immediate vicinity of the distal end (170) than in the configuration described above. This is considered to be within the scope of the invention and is illustrated in FIG. 7c (enlargement of the slant angle underneath reference numeral 170).

Figure 7D:
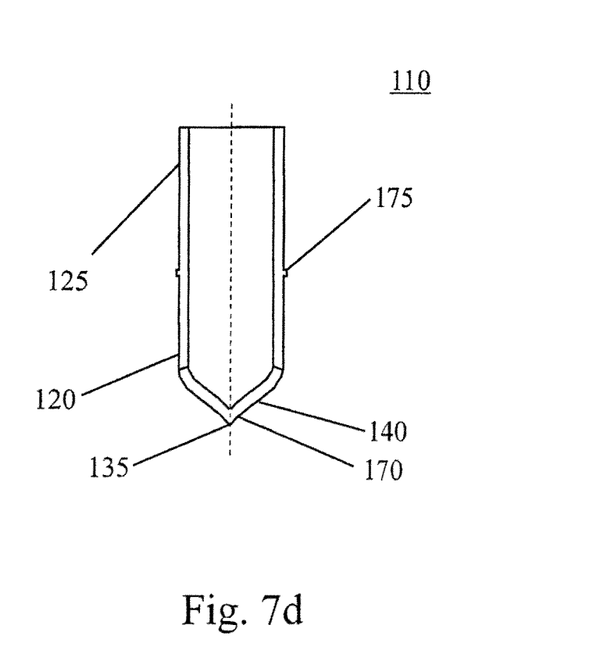

FIG. 7d shows another preferred embodiment of the invention as a cross-sectional view through the tube (110). At the distal end (170) is formed a point (135) to assist with the incision or the beginning of the separation of the opening area or the boundary region. The point (135) makes it possible to make an incision or penetrate the boundary region with reduced application of force compared with an endpiece that does not have a corresponding point. Advantageously, the point (135) is combined with one of the previous embodiments (from FIG. 7b, FIG. 7c), as shown in FIG. 7d. However, it is also possible according to the invention to combine the embodiment with a point having an endpiece with for example a constant slant angle α.

It is also possible to have embodiments according to the invention in which the opening area is detached completely from the remainder of the top. The top may either fall into the container or be removed from the container by other means.

In a preferred embodiment a dorsal end (125) of the tube (110) ensures that the end of the tube is lodged by frictional engagement in the top (30) of the container (20) when the opening tool (100) is in the applied position. For this purpose the upper end of the tube is slightly conical in shape, typically with an angle of about 0.5 to 5°, more typically about 0.7 to 4° and most typically about 1 to 3°. This cone serves a number of purposes. It smoothes out any unevenness in the cutting contour produced by the cutting edge and occurring during the incision into the opening area, by somewhat expanding the cutting contour. In this way the tube (110) or the opening tool (100) simultaneously forms a seal with the top (30) of the container (20), which at least partly prevents or reduces evaporation in the case of volatile reagents such as alcohol. Finally, the frictional engagement provides a stable mechanical fit of the tube in the top or container, with the result that there is no need for the positioning elements or similar elements for engagement or the like briefly described above.

If even greater stability is required compared with the friction-locked fit described above, the opening tool (100) may be equipped with at least one positioning element for accurately positioning it on the container (20). Typically, elements are selected from a group comprising pins, holes, slots, grooves and ridges. During the pressing action the positioning element engages with a mating positioning element as a counterpart which is provided on the container or on the top (30). Corresponding possible pairs consist of a pin and hole, pin and slot, groove and ridge or pin and groove, although combinations of other elements may also be taken into consideration within the scope of the invention.

The invention is also directed to an apparatus for carrying out the processes disclosed and comprises apparatus components for performing each of the process steps described. These process steps may be carried out using hardware components, a computer programmed with suitable software or any combination of the two, or by any other means. In addition, the invention is also directed to processes by which the apparatus described is operated. It comprises process steps for performing each function of the apparatus.

The invention claimed is:

1. System for removing a pipettable substance from a pre-filled container which is closed off by a top that has at least one opening area, said system comprising
    an opening tool, comprising
        (i) a plurality of tubes each of which has a cross-section substantially corresponding to a shape of an opening area from a pre-filled container and at a distal end of each of the plurality of tubes, an inclined endpiece extending substantially at an angle relative to a longitudinal axis of the plurality of tubes, which moves a part of the top located inside the opening area toward the container when the opening tool is applied so as to make an opening in the top,
        (ii) a point of attack for a transporting tool, the opening tool being designed to remain on the container after use,
    a transporting tool for moving the opening tool through the top, and
    a pipetting tool which is adapted to be inserted over at least part of a length thereof through the plurality of tubes into an interior of the container, in a position of use of the opening tool, and one end of which can be connected to a suction device for sucking a pipettable substance out of the interior of the container.

2. System according to claim 1, wherein the opening area is substantially of a shape selected from the group consisting of a circle, ellipse and polygon.

3. System according to claim 1, wherein the opening area comprises one or more features selected from the following group:
    a) the opening area has a substantially lesser material thickness than the top,
    b) the opening area comprises a different material from the top,
    c) the opening area is confined by a boundary region which substantially has a lesser material thickness than the top, and/or
    d) the opening area is confined by a boundary region of greater material thickness than the top.

4. System according to claim 1, wherein the opening tool and/or the container comprises at least one positioning element for exact positioning on the transporting tool.

5. System according to claim 1, wherein the inclined endpiece of the tubes have a point at a distal end thereof and have at least two different angles α relative to the longitudinal axis of the tube over the area from its dorsal end to said distal end, wherein at least one angle α is in the region of the distal end and at least one angle α is in the region of the dorsal end.

6. System according to claim 5, wherein the at least one angle α in the region of the distal end is substantially smaller than in other areas of the inclined endpiece.

7. System according to claim 1, wherein a dorsal end of the tubes ensures a friction-locked engagement of the tubes in the top with the opening tool in an applied position thereof.

8. System according to claim 1, wherein the plurality of tubes are arranged in an m×n matrix and connected by a common element.

9. System according to claim 8, wherein a spatial direction defined by the perpendicular to the main plane of the inclined endpiece of the tube is different in at least two of the tubes such that the tubes of the opening tool are at different angular positions relative to their longitudinal axes.

10. Process for removing a pipettable substance from a pre-filled container, comprising the steps of:

a) providing the system according to claim 1 and a container for holding pipettable substances, comprising:
   a plurality of similar or differently shaped chambers each having at least one opening,
   at least one top for closing off the opening,
   cone-like guides formed in the at least one top;
b) automatically or manually applying the opening tool to the top of the container,
c) moving the opening tool through the top of the container by the transporting tool so that the plurality of tubes of the opening tool at least partly opens the opening area in the top of the container and the plurality of tubes penetrate into an interior of the container, over at least part of its length, and is fixed therein,
d) positioning the pipetting tool in a position above a through-opening in the opening tool and lowering the pipetting tool into the through-opening and into the plurality of tubes below, until at least part of the pipetting tool projects from the distal end of each of the plurality of tubes into a pipettable substance that is to be removed,
e) sucking up the pipettable substance contained in the container through the pipetting tool by means of a suction device connected thereto.

11. Process according to claim 10, further comprising
f) total withdrawal of the pipetting tool from the opening tool.

12. Process according to claim 11, wherein d) to f) are repeated several times, using the same or different pipetting tools.

13. Process according to claim 10, wherein the movement in c) is accompanied by the engagement of positioning elements between the container and/or the opening tool and the transporting tool, which are selected from among the group consisting of pin—hole, pin—slot and groove—ridge.

14. Process according to claim 10, wherein d) to f) are carried out using a plurality of pipetting tools at the same time.

15. Process according to claim 10, wherein the container has a number of structurally separated chambers, each of which is assigned to at least one opening area in a top, and/or wherein in c) the plurality of tubes open a plurality of opening areas at least in part as the opening tool is moved.

16. Process according to claim 10, further comprising:
g) closing off the container with the opening tool applied by means of a cover arranged on the opening tool.

17. Process according to claim 10, wherein in b) the opening tool is centred on the top.

\* \* \* \* \*